(12) United States Patent
Anelli et al.

(10) Patent No.: US 9,795,695 B2
(45) Date of Patent: Oct. 24, 2017

(54) PROCESS FOR THE PREPARATION OF GADOBENATE DIMEGLUMINE COMPLEX IN A SOLID FORM

(71) Applicant: BRACCO IMAGING S.p.A., Milan (IT)

(72) Inventors: Pier Lucio Anelli, Milan (IT); Pierfrancesco Morosini, Vilanova del Sillaro (IT); Silvia Ceragioli, Milan (IT); Fulvio Uggeri, Codogno (IT); Luciano Lattuada, Bussero (IT); Roberta Fretta, Collegno (IT); Aurelia Ferrigato, Trecate (IT)

(73) Assignee: BRACCO IMAGING S.p.A., Milan (IT)

( * ) Notice: Subject to any disclaimer, the term of this patent is extended or adjusted under 35 U.S.C. 154(b) by 0 days.

(21) Appl. No.: 15/130,160

(22) Filed: Apr. 15, 2016

(65) Prior Publication Data

US 2016/0228583 A1 Aug. 11, 2016

Related U.S. Application Data

(62) Division of application No. 13/510,409, filed as application No. PCT/EP2010/067981 on May 17, 2012, now abandoned.

(30) Foreign Application Priority Data

Nov. 23, 2009 (EP) .................................. 09176713

(51) Int. Cl.
| | | |
|---|---|---|
| A61K 9/00 | (2006.01) | |
| A61K 49/18 | (2006.01) | |
| C07C 227/38 | (2006.01) | |
| B29C 67/24 | (2006.01) | |
| C07C 213/10 | (2006.01) | |
| C07C 227/40 | (2006.01) | |

(52) U.S. Cl.
CPC ........ *A61K 49/1887* (2013.01); *A61K 9/0019* (2013.01); *B29C 67/24* (2013.01); *C07C 213/10* (2013.01); *C07C 227/38* (2013.01); *C07C 227/40* (2013.01); *Y10T 428/2982* (2015.01)

(58) Field of Classification Search
CPC A61K 9/0019; A61K 49/1887; C07C 227/38; Y10T 428/2982; B29C 67/24
See application file for complete search history.

(56) References Cited

U.S. PATENT DOCUMENTS

| | | |
|---|---|---|
| 5,980,864 A | 11/1999 | Platzek et al. |
| 2004/0022732 A1 | 2/2004 | Zotz et al. |
| 2009/0118537 A1 | 5/2009 | Ceragioli et al. |
| 2009/0155181 A1 | 6/2009 | Rowe |

FOREIGN PATENT DOCUMENTS

| | | |
|---|---|---|
| AU | 620841 B2 | 2/1992 |
| CA | 2102461 A1 | 5/1994 |
| EP | 0230893 A2 | 8/1987 |
| EP | 0592306 A2 | 4/1994 |
| JP | S62-195388 A | 8/1987 |
| JP | H06-181890 A | 7/1994 |
| JP | H10-509424 A | 9/1998 |
| JP | 2009-507882 A | 2/2009 |
| RU | 2059642 C1 | 5/1996 |
| WO | 1996/10359 A1 | 4/1996 |
| WO | 2001-41816 A2 | 6/2001 |
| WO | 2003-026702 A1 | 4/2003 |
| WO | 2007/031390 A1 | 3/2007 |

OTHER PUBLICATIONS

Broadhead et al., The Spray Drying of Pharmaceuticals, Drug Development and Industry Pharmacy, vol. 1, Issue 11 & 12, pp. 1169-1206, published 1992.

Corrigan. O.I., "Thermal analysis of spray dried products", Thermochimica Acta, 1995, vol. 248, pp. 245-258, Elsevier Science BV.

De Haen, et al., "Gadobenate Dimeglumine 0.5 M Solution for Injection (MultiHance®): Pharmaceutical Formulation and Physicochemical Properties of a New Magnetic Resonance Imaging Contrast Medium," Journal of Computer Assisted Tomography, 23:S161-S168 (1999).

Ghaghada, Ketan B. et al., "New Dual Mode Gadolinium Nanoparticle Contrast Agent for Magnetic Resonance Imaging", PLoS One, vol. 4, No. 10, E7628, Oct. 29, 2009, pp. 1-7, XP002578359.

Huang, Lian-Feng et al., "Impact of solid state properties on developability assessment of drug candidates", Advanced Drug Delivery Reviews, 2004, vol. 56, pp. 321-334, Elsevier BV, doi:10.I016/j.addr.2003.10.007.

Kirchen et al., Safety assessment of gadobenate dimeglumine (MultiHance®): Extended clinical experience from phase I studies to post-marketing surveillance, Journal of Magnetic Resonance Imaging, vol. 14, Issue 3, pp. 281-294, Sep. 2001 ; first published online Aug. 23, 2001 (abstract).

"The MERCK Index: An Encyclopedia of Chemicals, rugs, and Biologicals", Thirteenth Edition, Section "G", reference No. 4344 'Gadobenate Dimeglumine', p. 767, Maryadele J. O'Neil, Senior Editor, Merck & Co., Inc., Whitehouse Station, NJ, 2001, Library of Congress Catalog. Card No. 89-60001, ISBN No. 0911910-13-1.

(Continued)

*Primary Examiner* — Yanzhi Zhang
(74) *Attorney, Agent, or Firm* — Vivicar Law, PLLC

(57) ABSTRACT

The present invention discloses a process for the preparation of gadobenate dimeglumine complex in a solid form. In particular, said solid form is conveniently obtained by spray-drying a corresponding liquid suspension at a given temperature and concentration. The present invention is particularly advantageous for the industrial scale as the solid form may be obtained by employing water as a solvent, which is a non-toxic solvent, easy to handle and basically not requiring troublesome health or safety precautions.

5 Claims, No Drawings

(56) References Cited

OTHER PUBLICATIONS

Mukuta, Takashi et al. "Crystallization Conditions of Crystal Agglomerates Suitable for Filtration Separation", Journal of the Society of Powdered Technology, 2006, vol. 43, No. 12, pp. 882-889 (including English translation).
Palermo, Joseph A., "Annual Review: Crystallization, Recent development of crystallization processes has emphasized equilibrium studies and the growth of single crystals", Industrial and Engineering Chemistry, 1968, vol. 60, No. 4, pp. 65-93.
Platzek, J. et al., "Synthesis and Structure of a New Macrocyclic Polyhydroxylated Gadolinium Chelate Used as a Contrast Agent for Magnetic Resonance Imaging", Inorganic Chemistry, 1997, vol. 36, No. 26, pp. 6086-6093, American Chemical Society.
Uggeri et al., "Novel Contrast Agents for Magnetic Resonance Imaging. Synthesis and Characterization of the Ligand BOPTA and Its Ln(III) Complexes (Ln=Gd, La, Lu). X-ray Structure of Disodium (TPS-9-145337286-C-S)-[4-Carboxy-5,8,11-tris(carboxymethyl)-1-phenyl-2-oxa-5,8,11-triazatridecan-13-oato(5-)]gadolinate(2-) in a Mixture with Its Enantiomer," Inorg. Chem., 34:633-642 (1995).
Office Action for Australian application No. 2010320832, dated Aug. 16, 2013.
Office Action for Canadian application No. 2,781,718, dated Jan. 28, 2014.
Office Action for Chinese application No. 201080059517.8, dated Apr. 1, 2013 (English translation).
Office Action for Chinese application No. 201080059517.8, dated Jan. 20, 2014 (English translation).
Office Action for Chinese application No. 201080059517.8, dated Sep. 23, 2014 (English translation).
Office Action for Chinese application No. 201080059517.8, dated Mar. 11, 2015 (English translation).
Office Action for Chinese application No. 201080059517.8, dated Nov. 20, 2015 (English Translation).
Office Action for Japanese application No. 2012-539358, dated Oct. 1, 2013 (English translation with Summary).
Office Action for Japanese application No. 2012-539358, dated Apr. 22, 2014 (English translation with Summary).
Office Action for Korean application No. 10-2012-7015988, dated May 4, 2015 (English Translation).
Office Action for New Zealand application No. 600334, dated Feb. 27, 2013.
Office Action for New Zealand application No. 600334, dated Jul. 2, 2014.
Office Action for New Zealand application No. 600334, dated Aug. 29, 2014.
Decision of Grant for Russian application No. 2012125964, dated Sep. 19, 2014 (English translation).
PCT International Preliminary Report on Patentability for PCT/EP2010/067981, dated May 3, 2012.
PCT International Search Report for PCT/EP2010/067981, dated Mar. 23, 2011.
Fan Biting, Chinese drugs pharmaceutics, Shanghai Science & Technology Press, Feb. 2000, p. 136.
Pan Yongkang, Modern Drying Technology, Chemical Industry Press, May 2007, p. 1030.
Decision of Reexamination for Chinese application No. 201080059517.8, dated Jan. 6, 2017 (English translation).
Notification of Reexamination for Chinese application No. 201080059517.8, dated Sep. 7, 2016 (English translation).
Yu Zixing, Pharmaceutical Chemical Engineering, Process and Device, China Medical Science Press, Dec. 1991, p. 373.
Office Action for Indian application No. 5400/CHENP/2012, dated Mar. 23, 2017.

PROCESS FOR THE PREPARATION OF GADOBENATE DIMEGLUMINE COMPLEX IN A SOLID FORM

CROSS-REFERENCE TO RELATED APPLICATIONS

This application is a divisional of U.S. patent application Ser. No. 13/510,409, filed May 17, 2012, which is the national stage application of corresponding international application number PCT/EP2010/067981, filed Nov. 23, 2010, which claims priority to and the benefit of European application no. EP09176713.7, filed Nov. 23, 2009, all of which are hereby incorporated by reference in their entirety.

The present invention relates to a process for the preparation of a solid form of a polyamino polycarboxylic gadolinium complex by a spray-drying procedure. The present process enables the collection of a solid form of the gadobenate dimeglumine complex which may be employed, for example, as a contrast agent in the diagnostic imaging field.

BACKGROUND

Contrast media are substances used to enhance the contrast of structures or fluid within the body in the medical imaging field. Among the imaging techniques currently employed, the magnetic resonance imaging (MRI) is one of the most relevant, due to its efficacy and safety and, in this prospect, several contrast media have been developed during the last decades. Said MRI contrast media comprise, basically, a paramagnetic metal (generally gadolinium) which is complexed with a poliammino carboxylic chelate, either cyclic or acyclic. Examples of said paramagnetic complexes are Gd-DTPA, Gd(HP-DO3A) and Gd-BOPTA. In particular, the physiologically compatible salt of this latter (i.e. the dimeglumine salt see The Merck Index, XII Ed., 2001, Nr 4344), referred also as gadobenate dimeglumine complex, of Formula I below, represents the active ingredient of one of the most commonly used MRI contrast agent, commercially known as MultiHance®.

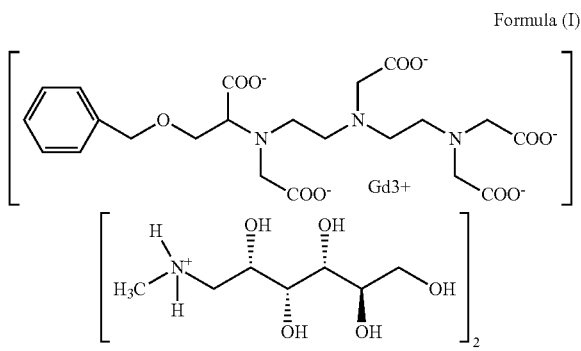

Formula (I)

MultiHance® is obtained for instance as disclosed in EP0230893.

It has to be noted that the degree of purity is for contrast agents, as well as for pharmaceutical compounds in general, of a critical issue. In particular for pharmaceutical compounds to be injected, quality standards are in fact very restricting to fully satisfy all the competent authorities requirements.

In the imaging field, accordingly, the contrast: agent has to be prepared in a pure, stable and convenient physical form and, in the most of the cases, this represents a crucial point and a challenge that any manufacturer has to face. A suitable physical form should be, for instance, the one that allows, first of all, a reliable and practical recovering of the compound in the final form ready to be administered, such to guarantee a safe and prolonged storage of the product.

In this respect, and whenever possible, the solid form of a chemical compound is generally preferred. In fact, when the product is obtained in a liquid or oily form or in a solution or suspension thereof, several isolation and purification techniques are further employed to convert such a product into the corresponding solid form (see for instance, Huang et al., Advanced Drug Delivery Reviews; 2004; 56; 321-334).

Among known processes, the selective precipitation from a proper solution, the evaporation of the solvent, the lyophilisation and the crystallization from a suitable organic solvent, or from a mixture of solvents, are some examples of methodologies widely used to this extent (see for example: TUMJ; 2001, 59(3), 53-59 and Palermo et al. Chemical Reviews; 1968; Vol. 60; 65-93).

The cited procedures, taken alone or even in any combination thereof, are currently employed, from the bench to the industrial scale, when a final solid form of a chemical compound is desirable or required, for example for workability reasons or for the preparation of a convenient solid drug dosage form. Typically, a filtration and a final drying step, usually under reduced pressure, are carried out in order to collect the product of choice as a dried solid (see for a general reference, Takashi et al. Journal of the Society of Powdered Technology, 2006; Vol. 43; No 12; 882-889).

Spray-drying technique represents an alternative method to the above, where a solid compound is collected starting from a proper solution (usually, an aqueous solution or a suspension of the same, by a spray-dryer device. This technique, however, suffers from some drawbacks, in particular when applied to molecules with specific chemical features, such as for instance, organic complexes or the like. In fact, some structural and/or chemical physical changes may be observed, including, among others, polymorphic changes, solvate formation or even undesirable glassy forms of the product (for a general reference, see for example, Corrigan et al., Thermochimica Acta 248; 1995; 245-258).

We have now surprisingly found that when a proper liquid composition of the gadobenate dimeglumine complex is subjected to a spray-drying procedure, the solid form thus obtained may be conveniently collected in high and reproducible yields and, noteworthy, said solid form substantially maintains the specifications of the starting liquid composition, even when the latter is intended for the administration and therefore in conformity with the limits and the specifications required for safety reasons.

SUMMARY OF THE INVENTION

The present invention discloses a process for the preparation of a solid form of the gadobenate dimeglumine compound, characterised in that a liquid composition of said compound undergoes a spray drying process.

Preferably, the liquid composition is an aqueous composition, more preferably a water solution, having a concentration of at least 0.2M, more preferably, comprised from 0.25M to 0.6M.

The liquid composition is fed to the spray-drying device and atomized preferably by using a two fluid nozzle or a pressure nozzle. The fed rate of the liquid composition depends on the type and on the scale of the equipment; as an example, and according to a preferred embodiment, it is set from about 5 g/min to about 13 g/min on a lab scale equipment, from about 2.5 to 8 kg/h on a pilot plant scale and from about 30 to 80 kg/h on an industrial scale plant.

The present process is preferably carried out at an inlet temperature (T-inlet) of the spray-drying device comprised from 140° C. to 280° C., whereas the out let temperature (T-outlet) has a value comprised from 70° C. to 120° C.

In another aspect, the invention relates to the gadobenate dimeglumine in the solid form, obtainable by the present spray-drying process. Preferably, the solid form thus obtained is a powder having an average particle size comprised from about 1 μm to about 200 μm, even more preferably, from about 20 μm to 70 μm.

In a further aspect, the present invention relates to a kit of parts comprising the gadobenate dimeglumine, obtained as a solid according to the present process, along with a physiological acceptable aqueous carrier.

Finally and according to an additional aspect, the present invention refers to a process for the preparation of a solid form of the BOPTA ligand, characterised by spray-drying a liquid solution of said compound.

DETAILED DESCRIPTION OF THE INVENTION

The present invention relates to a process for the preparation of a solid form of gadobenate dimeglumine compound of formula (I):

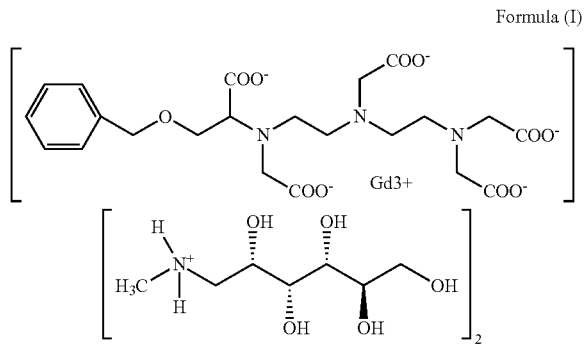

Formula (I)

comprising the spray-drying of a liquid composition of said compound. According to a preferred embodiment, in the spray-drying device, the liquid composition containing the active ingredient of Formula I is subjected to:
  i) an atomization step,
  ii) a drying operation inside the spray-drying chamber by using a co-current flow of a drying gas at a selected temperature, and finally
  iii) a collection step of the thus formed particles.

Unless otherwise provided, with the term "solid form" it is intended not solved or suspended in any media.

The term "atomization process" is intended to indicate the formation of micro-particles, usually in the form of micro-droplets or the like. By "micro particles" are meant particles having a mean diameter size comprised from about 10 μm to 600 μm.

The term "co-current flow" refers to a process where the sprayed composition and the drying gas pass through the dryer in the same direction, whilst the term "liquid composition" refers to a solution, or a suspension, of the selected compound in any appropriate solvent system, including e.g. organic and inorganic solvent and mixtures thereof.

Typical examples of said solvent systems are, inter alia, aqueous systems such as purified water (e.g. demineralised, distilled or deionised water and the like), or mixtures of water and water-miscible solvents. Examples of water-miscible solvents are, for instance, polar solvents, including, but not limited to, lower (e.g. $C_1$-$C_4$) alcohols, acetone, and the like. Preferably, the liquid composition is an aqueous composition, more preferably water, even more preferably, purified water.

The gadobenate dimeglumine of Formula I is present in the above liquid composition in any proper amount, for example so that the nozzle obstruction is prevented. Preferred concentrations are of at least 0.2 M, more preferably from about 0.25 M to about 0.6 M, more preferably from about 0.45 M to about 0.55 M (with M meaning the molarity of the solution).

In more detail, in the present process the liquid composition is preferably fed to the apparatus at a temperature from 15° C. to 40° C., more preferably, from about 20° C. to about 25° C., and submitted to an atomization process in the spray-dryer chamber according to the above step i), by using a known atomisation device (located for example at the top of said chamber). Examples of suitable atomization devices comprise, among others, a pressure, a rotary, or a two fluid nozzle. Particularly preferred are either the two fluid nozzle or the pressure nozzle.

As regards the liquid composition fed rate, preferred values for a lab scale equipment are, from about 5 to 13 g/min, more preferably from about 8 to 10 g/min, whereas in case of an employment of the present process in a pilot plant, the feed rate may be comprised from 2500 and 8000 g/h, preferably around 2800-3200 g/h, whereas in case of industrial applications, the fed rate may range from 30 to 80 kg/h, preferably, from 35 to 45 kg/h.

By "lab scale" it is intended to refer to amounts of compound up to about 1 Kg, whereas the terms "pilot plant" and "industrial plant" refer to amounts typically from 1 Kg to 10 kg for the former, and more than 10 Kg for the latter.

The thus atomised liquid composition is then dried in the device by using a co-current flow of a drying gas used in the art for similar procedures, such as, for instance, air or nitrogen. According to the invention the inlet temperatures of the gas (herein referred as T-inlet) is from about 140° C. to 280° C., preferably the inlet temperature is from 160° C. to 200° C.

Accordingly, the outlet temperature (herein indicated as T-outlet) of the gas is from about 70° C. to about 120° C.

The gadobenate dimeglumine is finally recovered in a solid form, preferably by passing through a cyclone, in high yields of conversion (up to 98%) and with a content of residual water comprised between about 0.7% and about 5.5% (calculated by Karl Fisher titration and herein indicated as KF) as detailed in the experimental part herein below.

The process may be carried out by using a spray-drying equipment or plant, selected from those commercially available, such as, for instance, LAB PLANT SD 04 spray dryer or, alternatively in case of industrial scale amounts, a MOBILE MINOR™ pilot plant.

As regards to the starting material, a liquid composition of the gadobenate dimeglumine might be easily prepared by reacting the polyamino carboxylic derivative 4-carboxy-5,8,11-tris(carboxymethyl1)-1-phenyl-2-oxa-5,8,11-triazatridecan-13-oic acid (BOPTA) as the ligand, with $Gd_2O_3$ and N-methyl-glucamine (meglumine), as disclosed, for example, in EP 0230893 (Bracco Ind Chimica).

Both $Gd_2O_3$ and meglumine are commercially available, e.g. from Sigma-Aldrich (PN 278513 and M9179 respectively), whereas the BOPTA ligand may be prepared according to methods known to the ordinary practitioner, e.g. as disclosed in WO 2007/031390 (Bracco Imaging SpA).

It is worth noting that the present process for the preparation of gadobenate dimeglumine by spray-draying is particularly advantageous for the industrial scale as the spray-dried form may be obtained by employing water as a solvent, which is easy to handle and basically not requiring troublesome health or safety precautions. Finally, the overall process time is also very convenient; for example, in case of a lab scale equipment, the spray drying process allows to obtain up to 6-7 g/min of solid gadobenate, whereas in case of an industrial scale plant, up to 40 Kg/h may be obtained.

As evident from the experimental part herein below (see in particular Example 2: comparative examples), the process of the present invention advantageously enables the preparation of a suitable solid form of the gadobenate dimeglumine, in a solid form different from the one obtainable by using other commonly employed methodologies leading to solid forms with unfavourable handling, workability (gummy, sticky or glassy solids), and extremely low recovering yields, due to cumbersome and time consuming procedures required for their collection.

Therefore, and according to a further aspect, the present invention relates to the spray-dried form of gadobenate dimeglumine obtainable by the present spray-drying process.

The solid form of the present invention, in particular, presents characteristic features such as a good flowability, a good stability (up to 2 years when properly stored, i.e. under inert atmosphere) and a good wettability and dissolution rate (the solid form is soluble in water even at room temperature in a very short frame of time, e.g. few seconds) along with a controlled average particle size (misured by using a laser light scattering technique, and indicated with D(v,0.5), which means the equivalent diameter of the 50% of population, expressed as volume distribution).

In fact, by using the preferred ranges of the operative conditions of the spray drying process above disclosed, the obtained solid form of the gadobenate dimeglumine is characterised in that it is a stable water soluble powder having a particle size from 1 µm to 200 µm.

Preferably, the powdered gadobenate is obtained as a powder having a particle size comprised from 10 µm to 150 µm, by spray-drying a solution of gadobenate having a concentration from 0.2M to 0.8M, at an inlet temperature comprised from 100° C. to 250° C.

Even more preferably, the spray-dried gadobenate is obtained as a powder having a particle size ranging from about 20 µm to about 70 µm.

Said range is conveniently obtained, preferably by spray drying a solution of gadobenate having a concentration comprised from 0.45M to 0.55M, at an inlet temperature from 160° C. to 180° C., by using a pressure nozzle. Even further, the solid product obtained by the present process shows a high final quality (up to 99.9% of purity, according to HPLC data), as no impurity formation or thermal degradation is detected throughout the process, along with an excellent water dissolution rate. To this extent, it has to be noted that the powdered gadobenate obtained according to the present invention has optimal dissolution characteristics, requiring less than 1 mL of water 1 g of product at room temperature (i.e. at a temperature comprised from 20° C. to 30° C.), readily occurring in less than one minute.

Whenever required, the solid product may be appropriately stored using precautions known in the art (e.g. protective packaging such as moisture proof bags), satisfactorily avoiding the formation of side products or alterations of the physical-chemical properties of the solid. In this direction, it has been observed that the powdery solid form thus obtained may be conveniently stored even for 2 years, retaining the required degree of purity and the initial physical properties, such as colour, solubility and the like.

The present solid form, may be readily used, in the preparation of pharmaceutical compositions, such as an injectable formulation to be used as MRI contrast agent.

In a further aspect of the present invention, the solid gadobenate dimeglumine of Formula I obtained by the present process is packaged in a two component kit, preferably for administration by injection. The kit may comprise a first container, containing the spray-dried gadobenate dimeglumine, and a second container, containing a physiologically acceptable aqueous carrier. Examples of suitable carries are water, typically sterile, pyrogens free water (also generally indicated as water for injection), aqueous solution such as saline (which may advantageously be balanced so that the final product for injection is not hypotonic), or aqueous solutions of one or more tonicity adjusting substances such as salts or sugars, sugar alcohol, glycols or other non-ionic polyol materials (e.g. glucose, sucrose, glycerol, glycols and the like). Said two component kits can include two separate containers or a dual-chamber container. In the former case the container is preferably a conventional septum-sealed vial, wherein the vial containing the solid residue is sealed with a septum through which the liquid carrier may be injected using an optionally prefilled syringe. In such a case, the syringe used as the container of the second component is also used then for injecting the contrast agent. In the latter case, the dual chamber container is preferably a dual chamber syringe and once the solid has been reconstituted and then suitably mixed or gently shaken, the container can be used directly for injecting the contrast agent.

According to a further aspect, the invention relates to the preparation of the kit, wherein the first container comprises aliquots of the spray-dried gadobenate dimeglumine according to the process described above, followed by combination with a second container comprising aliquots of the suitable solvent, to achieve a kit of parts embodiment, ready for preparation of the injectable contrast agent.

Even further, and according to an additional aspect, the present invention relies on a process for the preparation of a solid form of 4-carboxy-5,8,11-tris(carboxymethyl1)-1-phenyl-2-oxa-5,8,11-triazatridecan-13-oic acid (BOPTA ligand, see formula II below), characterized by spray-drying a liquid composition of said compound.

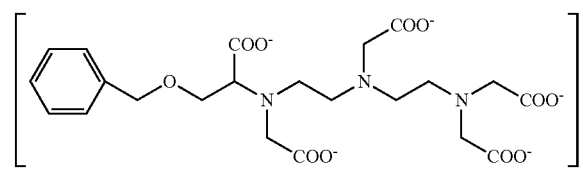

Formula (II)

In this respect, it is known in the art the preparation of a solid form of the BOPTA by multiple crystallizations from acetone/water, next to the elution on a chromatographic resin, as disclosed, for instance, in WO 2007/031390 (Bracco Imaging SpA). In particular, said procedure contemplates first the isolation of the wet solid BOPTA, and then the final drying step under controlled temperature to obtain a final solid product with a satisfactory solvent content.

Alternatively, we have now found that the isolation of BOPTA in a convenient: dried solid form may be achieved by dissolution of the aforementioned wet solid BOPTA in an aqueous medium, so to obtain an aqueous liquid composition, and submitting the latter to a spray-drying procedure. By that, the dried solid BOPTA may be readily collected in a short timerame, avoiding the drying step, as formerly reported.

Unless otherwise provided, said process may be conveniently performed substantially using the same devices and conditions as previously described for the gadobenate dimeglumine spray-drying.

By analogy, the term "liquid composition" in this further aspect of the invention has the e meaning as above, i.e. a solution, or even a suspension, of the selected compound (in this case BOPTA) in any appropriate solvent system, as afore mentioned Accordingly, a suitable BOPTA liquid composition for the spray-drying process may be obtained by dissolution of the wet BOPTA obtained according to WO2007/031390 (Bracco Imaging SpA) in a proper solvent system, as previously contemplated for the gadobenate dimeglumine spray-drying process.

Thus, the isolation of the solid BOPTA may be carried out by spray-drying a corresponding liquid solution with a concentration preferably ranging from 7% w/w to 14% w/w (where % w/w means the mass percentage of the compound with respect to the mass of the total composition), at an inlet temperature of the device preferably selected from about 120° C. to 160° C., and an outlet temperature from about 60° C. to 95° C.

The feed rate of the liquid composition preferably selected from about 1200 g/h to 2400 g/h at a feed temperature ranging from approximately 40° C. to 50° C., by using, for instance, a MOBILE MINOR™ pilot plant.

The collected solid BOPTA may be conveniently used, for example, in the preparation of paramagnetic complexes, e.g. in the preparation of the previous mentioned gadobenate dimeglumine, by procedures known in the art and formerly reported.

As set forth in the experimental part herein below, all of the obtained data clearly support the consistency and reliability of the process of the present invention, being intended for the preparation of a solid form of gadobenate dimeglumine of Formula I, by spray-drying a corresponding liquid, preferably aqueous, solution. Moreover, the solid form obtained by the present process, has peculiar features (e.g. high stability, purity and dissolution rate) that readily allow its isolation and storage, as well as its inclusion in a pharmaceutical kits. The invention will be now illustrated in more details by the Examples reported in the following Experimental Part, not to be intended as a limitation of the scope of the invention.

EXPERIMENTAL PART

Example 1: Solid form of Gadobenate Dimeglumine (Formula I) Obtained by Spray-Drying Spray-Drying Devices Employed:
LAB PLANT SD04 spray dryer with co-current flow, equipped with a two fluid nozzle.
MOBILE MINOR™ pilot plant, with co-current flow and equipped with two fluid nozzle or pressure nozzle.
SD size 12.5 plant, with co-current flow and equipped with pressure nozzle.
Gadobenate Dimeglumine, General Spray-Drying Procedure.

The solution was fed to the spray-drying device at room temperature through a two fluid nozzle or pressure nozzle, which was located at the top of the chamber, and atomized into the chamber.

At the same time a hot air flow was blown into the chamber to dry the atomised particles.

The powder thus generated were subsequently separated from the exhausted air flow by collection through a cyclone.

The solid was gathered in a sample collector located at the bottom of the chamber.

Different conditions (Examples 1a-g) were tested to optimize the process variables and also to support the reliability of the present process.

Example 1a 842 g of a 0.485 M aqueous solution of gadobenate dimeglumine of Formula I was fed to Lab Plant SD04 using the following parameters:
T-inlet 160° C.
T-outlet 87° C.
Feed rate: 8 g/min
310 g of gadobenate dimeglumine as white powder was obtained (yield 85%; KF 2.23%).

Example 1b 804 g of a 0.530 M aqueous solution of gadobenate dimeglumine of Formula I was fed to Lab Plant SD04 using the following parameters:
T-inlet 160° C.
T-outlet 88° C.
Feed rate 8.8 g/min
333 g of gadobenate dimeglumine as white powder was obtained (yield 91%; KF 1.74%).

Example 1c 790 g of a 0.348 M aqueous solution of gadobenate dimeglumine of Formula I fed to Lab Plant SD04 using the following parameters:
T-inlet 160° C.
T-outlet 88° C.
Feed rate 5.9 g/min
208 g of gadobenate dimeglumine as white powder was obtained (yield 81.5%; KF 1.36%).

Example 1d 608 g of a 0.535 M aqueous solution of gadobenate dimeglumine of Formula I was fed to Lab Plant SD04 using the following parameters:

T-inlet 195° C.
T-outlet 95° C.
Feed rate 6.1 g/min
232 g of gadobenate dimeglumine as white powder was obtained (yield 83.4%; KF 2.9596).

Example 1e 1300 g of a 0.5 M aqueous solution of gadobenate dimeglumine of Formula I was fed to MOBILE MINOR™ pilot plant using the following parameters:
T-inlet 190° C.
T-outlet 100° C.
Feed rate 3.9 kg/h
406.1 g of gadobenate dimeglumine as white powder was obtained (yield 97%; KF 2.6%).

Example 1f 1500 g of a 0.5 M aqueous solution of gadobenate dimeglumine of Formula I was fed to MOBILE MINOR™ pilot plant using the following parameters:
T-inlet 150° C.
T-outlet 80° C.
Feed rate 3.0 kg/h
608.3 g of gadobenate dimeglumine as white powder was obtained (yield 94%; KF 2.2%).

Example 1g 198 kg of a 0.48 M aqueous solution of gadobenate dimeglumine of Formula I was fed to a spray dryer SD size 12.5 plant using the following parameters:
T-inlet 170° C.
T-outlet 100° C.
Feed rate 40.0 kg/h
75.6 kg of gadobenate dimeglumine as white powder was obtained (yield 91%; KF 1.7%).

The powdered gadobenate obtained according to Examples 1a-g could be easily dissolved in an aqueous solution in a very short frame of time as indicated in the above description.

Example 2: Comparative Examples

Solid form of gadobenate dimeglumine of Formula I obtained by alternative procedures Comparative Example 2a: Isolation by Water Evaporation In a 1 L reactor, BOPTA (73.5 g; 143 mmol), N-methylglucamine (5.0 g; 271 mmol) and water (700 mL) were stirred at 50° C. until complete dissolution. $Gd_2O_3$ (26.15 g; 72.1 mmol) was added and the suspension was stirred at 80° C. for 75 min. At the end the mixture was filtered, the pH was adjusted to 7 and the solution was evaporated under vacuum to give a sticky glue-like residue.

The residue was dried at 25° C. under vacuum (1 mmHg) with $P_2O_5$ obtaining a glassy hard solid difficult to collect and, in case, to re-dissolve, due to its hardness.

Comparative Example 2b: Isolation by Lyophilization 100 mL of a 0.5 M aqueous solution of gadobenate dimeglumine (prepared according to the procedure described in the Comparative Example 2a) were lyophilized using a Christ Alpha 1-4 lyophilizer for 24 h to give a glassy solid, whose recovery was troublesome and unprofitable, especially when applied to industrial scale amounts.

Comparative Example 2c: Isolation by Precipitation 5 mL of a 0.5 M gadobenate dimeglumine solution (prepared according to the procedure described in the Comparative Example 2a) were added dropwise to 100 mL of 2-propanol, under stirring at room temperature.
A sticky gummy solid was obtained by precipitation into the reactor and its recovery was problematic and annoying due to the unfavourable consistency of the solid form.

Comparative Example 2d: Isolation by Precipitation 4 mL of a 0.5 M gadobenate dimeglumine solution (prepared according to the procedure described in the Comparative Example 2a) were added dropwise to 100 mL of ethanol kept under stirring at room temperature.
A white gummy solid was obtained by precipitation, but also in this case, its recovery was problematic and annoying due to the unfavourable consistency of the solid form.

Example 3: Solid Form of the BOPTA Ligand (Formula II) Obtained by Spray-Drying

Spray-Drying Device:
MOBILE MINOR™ pilot plant with co-current flow and equipped with two fluid nozzle or pressure nozzle
BOPTA General Spray-Drying Procedure
The same general procedure as the above gadobenate dimeglumine spray-drying procedure has been followed.
An aqueous suspension or solution of the BOPTA ligand was fed to the spray-dryer at a temperature of about 45-50° C., with a co-current flow of air and equipped with two fluid nozzle.

The aqueous suspension or solution of the BOPTA ligand was obtained by solving an appropriate amount of wet solid BOPTA in an aqueous medium.
The wet solid BOPTA is obtained by working in analogy to what disclosed in the afore mentioned WO2007/031390.
As a general reference, 452 g of an aqueous solution of the carboxylate sodium salt of N-[2-[(2-aminoethyl)amino] ethyl]-O-(phenylmethyl)serine (0.43 mol) were charged in a vessel of 3 L with 92 mL of water. The solution was heated to 55° C. and reacted with 356 g of an 80% bromoacetic acid aqueous solution. The pH was kept at 11-12 by 0% (w/w) sodium hydroxide solution. The reaction was completed in about 5 h at 55° C. and pH 11-12. The solution was cooled to 25° C. and pH was adjusted to 5.5 with 34% HCl so to lead to an aqueous solution of the titled compound which was eluted on a chromatographic resin, concentrated, acidified and subsequently crystallized. After filtration, the wet solid obtained was dissolved in a proper amount of water and then subjected to a spray-drying procedure to get a final dried solid BOPTA.

Example 3a 920 g of a 14.0% (w/w) BOPTA solution was fed to MOBILE MINOR™ pilot plant at 50° C. using the following parameters:
T-inlet 160° C.
T-outlet 73° C.
Feed rate 2400 g/h 121.5 g of BOPTA as white powder was obtained (yield 94%; KF 1.5%).

Example 3b 930 g of a BOPTA suspension (14% w/w) was fed to MOBILE MINOR™ pilot plant at 45° C. using the following parameters:
T-inlet 140° C.
T-outlet 72° C.
Feed rate 1750 g/h
93.8 g of BOPTA as white powder was obtained (yield 72%; KF 1.9%).

The invention claimed is:

1. A process for the preparation of a solid, pharmaceutical form of gadobenate dimeglumine compound of formula (I):

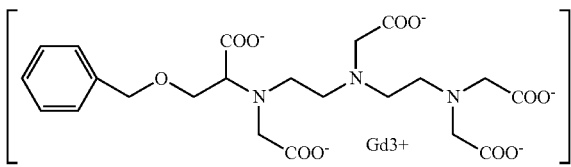

Formula (I)

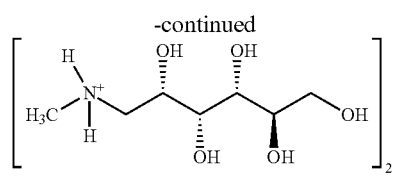

-continued comprising spray-drying an aqueous composition of said compound, wherein the form is a stable water soluble powder having a particle size from 1 μm to 200 μm, wherein said aqueous composition has a concentration from 0.2 M to 0.8 M gadobenate dimeglumine, and wherein the inlet temperature (T-inlet) of the spray-drier is comprised from 140° C. to 200° C. and the outlet temperature (T-outlet) is comprised from 70° C. to 120° C.

2. The process according to claim 1, wherein said concentration is comprised from 0.45 M to 0.55 M.

3. The process according to claim 1, wherein said aqueous composition is a purified water solution.

4. The process according to claim 1, comprising an atomization of the aqueous composition by using a pressure or a two-fluid nozzle.

5. The process according to claim 3, comprising an atomization of the aqueous composition by using a pressure or a two-fluid nozzle.

* * * * *